(12) United States Patent
Frazier (10) Patent No.: US 9,089,870 B2
(45) Date of Patent: Jul. 28, 2015

(54) SINGLE AND MULTIPLE USE APPLICATOR FOR VOLATILE FLUIDS HAVING A PROTECTIVE DEVICE FOR GUARDING AGAINST BEING CUT BY GLASS SHARDS FORMED WITHIN THE APPLICATOR

(71) Applicant: Thomas G. Frazier, Doylestown, PA (US)

(72) Inventor: Thomas G. Frazier, Doylestown, PA (US)

( * ) Notice: Subject to any disclaimer, the term of this patent is extended or adjusted under 35 U.S.C. 154(b) by 96 days.

(21) Appl. No.: 13/927,614

(22) Filed: Jun. 26, 2013

(65) Prior Publication Data

US 2014/0003858 A1 Jan. 2, 2014

Related U.S. Application Data

(60) Provisional application No. 61/665,141, filed on Jun. 27, 2012.

(51) Int. Cl.
| | |
|---|---|
| *A46B 11/02* | (2006.01) |
| *B05C 17/00* | (2006.01) |
| *A46B 11/00* | (2006.01) |
| *A61F 13/40* | (2006.01) |

(52) U.S. Cl.
CPC ............ *B05C 17/00* (2013.01); *A46B 11/0003* (2013.01); *A46B 11/0013* (2013.01); *A46B 11/0089* (2013.01); *A46B 2200/20* (2013.01); *A61M 35/006* (2013.01)

(58) Field of Classification Search
CPC .................................................. A61M 35/006
USPC ................................................ 401/132, 133
See application file for complete search history.

(56) References Cited

U.S. PATENT DOCUMENTS

| | | | |
|---|---|---|---|
| 4,304,579 A | | 12/1981 | Granville et al. |
| 4,304,869 A | * | 12/1981 | Dyke .......................... 435/287.6 |
| 4,572,689 A | * | 2/1986 | Chernack ...................... 401/132 |
| 4,586,106 A | | 4/1986 | Frazier |
| D289,999 S | | 5/1987 | Frazier |
| 4,677,521 A | | 6/1987 | Frazier |
| 4,937,910 A | | 7/1990 | Frazier |

(Continued)

OTHER PUBLICATIONS

The International Search Report and the Written Opinion of the International Searching Authority, or the Declaration for International Application No. PCT/US13/47635.

*Primary Examiner* — David Walczak
*Assistant Examiner* — Joshua Wiljanen
(74) *Attorney, Agent, or Firm* — John F. A. Earley, III; Frank J. Bonini, Jr.; Harding, Earley, Follmer & Frailey, P.C.

(57) ABSTRACT

The inventive applicator has a pliable plastic tube for holding a hermetically sealed crushable glass ampoule containing fluid to be dispensed from the applicator and applied by the applicator to a surface, and a pliable dispensing member mounted onto the plastic tube. The dispensing member has a dauber from which the fluid is dispensed and a protective device which surrounds a portion of the tube and is squeezed inwardly between the user's forefinger and thumb to cause the portion of the tube positioned thereunder to deform inwardly and crush the crushable glass ampoule positioned within the tube to release the fluid contained within the ampoule. The protective device guards against and minimizes the chances of users being cut by glass shards of the crushed glass ampoule when the protective device is subsequently squeezed inwardly to cause the fluid to move through the applicator to the dauber.

25 Claims, 9 Drawing Sheets

(56) References Cited

U.S. PATENT DOCUMENTS

| | | |
|---|---|---|
| D320,229 S | 9/1991 | Frazier |
| 5,098,297 A * | 3/1992 | Chari et al. .................. 433/215 |
| D351,106 S | 10/1994 | Frazier |
| 5,445,462 A * | 8/1995 | Johnson et al. ............... 401/132 |
| 5,509,744 A | 4/1996 | Frazier |
| D373,384 S | 9/1996 | Frazier |
| D413,730 S | 9/1999 | Frazier |
| D416,389 S | 11/1999 | Frazier |
| 6,039,488 A * | 3/2000 | Krawczyk et al. ............ 401/132 |
| 6,056,737 A | 5/2000 | Rosen |
| 6,254,297 B1 | 7/2001 | Frazier |
| 6,340,097 B1 * | 1/2002 | D'Alessio et al. ............ 401/132 |
| 6,367,115 B1 | 4/2002 | Frazier |
| D469,232 S | 1/2003 | Frazier |
| 6,729,786 B1 | 5/2004 | Tufts |
| 6,755,586 B1 | 6/2004 | Frazier |
| D495,843 S | 9/2004 | Frazier |
| 7,004,657 B2 | 2/2006 | Frazier |
| 7,727,175 B2 * | 6/2010 | Voegele .......................... 602/79 |
| 2014/0301765 A1 * | 10/2014 | Maiwald et al. .............. 401/132 |

* cited by examiner

SINGLE AND MULTIPLE USE APPLICATOR FOR VOLATILE FLUIDS HAVING A PROTECTIVE DEVICE FOR GUARDING AGAINST BEING CUT BY GLASS SHARDS FORMED WITHIN THE APPLICATOR

FIELD OF THE INVENTION

This invention relates to applicators for dispensing fluid therefrom and applying said fluid to a surface, and more particularly concerns applicators, such as the applicators of Frazier U.S. Pat. Nos. 7,004,657 and 6,254,297, both of which are hereby incorporated herein by reference, having a hermetically sealed crushable glass ampoule, which contains the fluid to be dispensed from the applicator and applied by the applicator to a surface, positioned within a deformable or pliant plastic tube which is closed at one end and which has a porous application tip at the other end, the fluid contained within the ampoule being released from the ampoule, when it desired to use the applicator, by squeezing the plastic tube inwardly to crush the glass ampoule contained therein.

BACKGROUND OF THE INVENTION

The use of sealed glass ampoules containing any number of volatile fluids is well known in the liquid applicator field. Typically, the applicator comprises a deformable/pliable plastic tube, an application tip, a filled ampoule (that is, a hermetically sealed crushable glass ampoule filled with the fluid to be dispensed from the applicator and applied by the applicator to a surface), and optionally a closure cap mountable onto the applicator for covering the application tip when the applicator is not in use. Such an applicator is sealed together such that after the fluid contained within the ampoule is released from the ampoule by the user of the applicator squeezing the tube inwardly using his forefinger and thumb to crush the glass ampoule contained therein, the fluid may be directed to the porous application tip. Depending on the physical attributes of the tube, occasionally a glass shard from the crushed ampoule may penetrate through the tube, causing injury to the user of the applicator by cutting into the user's finger and/or thumb, when the user subsequently squeezes the tube inwardly, after the fluid contained in the ampoule is released from the ampoule due to the ampoule being crushed, to cause the fluid released from the ampoule to flow to the applicator tip and be metered out from the applicator tip onto a surface.

In an attempt to prevent such an injury, wing-like pairs of gripping members and an extended breaking lever, which are described in U.S. Pat. Nos. 6,729,786, 6,536,975, and a U.S. patent application published under Publication No. US2006/0072959 A1, have been used to break the sealed ampoule. However, such devices have shortcomings, such as being cumbersome to use and non-ergonomic, in part due to such devices requiring that the tubes be constructed using rigid resins to permit the use of wing-like pairs of gripping members or the use of an extended breaking lever to effectively crush the ampoule, such rigid resin construction of the tubes making it difficult if not impossible to effectively control and vary the amount of fluid metered out from the applicator onto a surface by squeezing the tubes. Further, such devices are limited to the size and shape of the specific ampoule to be used that must match the internal confines of the device. To accommodate larger or smaller fills (that is, larger ampoules having larger amounts of fluid or smaller ampoules having smaller amounts of fluids), for example, a whole new device must be made, increasing the costs of tooling in an injected molded applicator shell. Another shortcoming of such devices is that they do not effectively provide for multiple applications of volatile fluids over time. That is, such devices do not effectively provide for multiple applications of volatile fluids over an extended period of time, such as a week or more, by failing to prevent drying out of the applicator tips and/or by failing to prevent the fluid from undertaking an unintended chemical reaction due to atmospheric exposure of the fluid on their daubers.

SUMMARY OF THE INVENTION

It is an object of the invention to provide an applicator that effectively provides for multiple applications of volatile fluid from the applicator to surfaces over time (e.g., over the course of a week or more), by providing a cap that effectively guards against the applicator tip from drying out and/or that guards against the fluid undergoing a premature, unintended, and/or undesired chemical reaction, such as one triggered by being exposed to the atmosphere.

Another object of the invention to provide an applicator that minimizes the chances of a user of the applicator being injured by a glass shard, created when a glass ampoule positioned in the applicator and containing the fluid to be dispensed from the applicator and applied by the applicator to a surface is crushed to release the fluid from the ampoule, penetrating through the tube and cutting the user's forefinger and/or thumb when the user squeezes the tube inwardly using his forefinger and thumb to cause the fluid released from the ampoule to flow to the applicator tip and be meter out from the applicator tip onto a surface.

It is another object of the invention to provide an applicator that may accommodate various amounts of fluid fills (that is, different volumetric amounts of fluid) to be contained within the applicator.

These and other objects are accomplished by my invention, the description of which is set out below. In a preferred embodiment of my inventive applicator, the applicator has basically a two-piece design, which is defined by a plastic tube for holding a hermetically sealed crushable glass ampoule containing the fluid to be dispensed from the applicator and applied by the applicator to a surface, and a dispensing member having a protective device, which surrounds a portion of the tube and is squeezed inwardly between the user's forefinger and thumb to cause the portion of the tube positioned thereunder to deform inwardly and crush the crushable glass ampoule positioned within the tube to release the fluid contained within the ampoule. The dispensing member having the protective device guards against and minimizes the chances of users being cut by glass shards since the protective device, which is squeezed inwardly by the user using his forefinger and thumb to cause the portion of the tube positioned thereunder to deform and crush the ampoule contained in the tube to release the fluid contained within the ampoule, substantially blocks any glass shards created when the crushable glass ampoule is crushed from penetrating outwardly from the applicator at the location of the protective device of the dispensing member when the applicator is subsequently squeezed at the protective device between the user's forefinger and thumb to direct the fluid released from the glass ampoule to the applicator tip and meter the fluid out from the applicator tip onto a surface. This two-piece design also allows an infinite number of ampoule holding tubes to be used to accommodate smaller or larger fluid (e.g., liquid) fills for the applicator using the same guard "head" (that is, the same dispensing member) of the applicator.

The pen-like design of my invention is an improvement in the art, providing a more ergonomic solution to problems encountered by single and multi-use applicators in the applicator field, as well as providing a more cost efficient applicator.

Further, my invention allows for the use of softer, more pliable resins than those typically used for prior art applicators to be used in manufacturing my applicator, making "activation" (that is, squeezing inwardly to cause the glass ampoule to be crushed) of my new applicator easier. In contrast to my inventive applicator, the use of such softer resins in prior art applicators that use wing-like pairs of gripping members or an extended breaking lever results in non-performance of the wing-like pair of gripping members and the extended breaking lever to activate the applicator, that is, to break the glass ampoule positioned in the applicator. Moreover, the use of more pliable resins in the tube and the dispensing member of my invention, as opposed to the rigid resins typically used for prior art applicators, facilitates effective metering of fluid out from my applicator to a surface. The use of soft pliable resins for the tube and dispensing member of my invention results in a tube and a dispensing member that are pliable to the extent that the tube and dispensing member of the invention are very responsive to the force placed on them by the user squeezing the protective device between the user's forefinger and thumb such that the amount of fluid dispensed from my applicator may be easily controlled by how much force the user creates squeezing the protective device between his forefinger and thumb. The ability to easily control and vary the flow rate of fluid being metered out from prior art applicators is hindered due to being constructed of rigid resins, which results in applicators that are hard to squeeze to meter out fluid therefrom. If the user only wishes that a small amount of fluid be dispensed from my applicator, the user only needs to squeeze the protective device lightly, until the desired amount of fluid is dispensed from my applicator where upon the squeezing of my applicator may be stopped, and if the user wishes to create a larger flow of fluid from my dispenser, he need only squeeze my applicator harder at the protective device to cause a larger flow of fluid from my applicator until the desired amount of fluid is dispensed from my applicator where upon the squeezing of my applicator may be stopped. The flow of fluid from my applicator may be varied by merely varying the amount "squeeze" force applied to my applicator by the user squeezing my applicator at the protective device, a light squeeze creating a low flow rate of fluid from my applicator and a more forceful squeeze creating a high flow rate of fluid from my applicator.

DETAILED DESCRIPTION

Turning now to the drawings, various preferred embodiments of my invention are shown. It should of course be understood that the description and drawings described herein are merely illustrative, and that various modifications and changes may be made in the structures disclosed without departing from the spirit of the invention. Like numerals refer to like parts through the several views.

FIGS. 1-4, 18, and 22-24 illustrate a first preferred embodiment of my inventive applicator 11, constructed in accordance with the invention, for dispensing fluid therefrom and applying said fluid to a surface. Applicator 11 has a deformable, pliable tube 13, preferably cylindrical in shape and preferably constructed from plastic material, such as a chemically inert resin such as polyethylene resins or ethylvinylacetate, or olefinic thermoplastic elastomers, using injection molding, for holding a crushable glass ampoule 15 containing a fluid 16 to be dispensed from the applicator 11. The tube 13 is capable of being readily deformed by finger pressure of the user of the applicator 11, and preferably returns to its original shape upon pressure release.

Figures 1, 2:
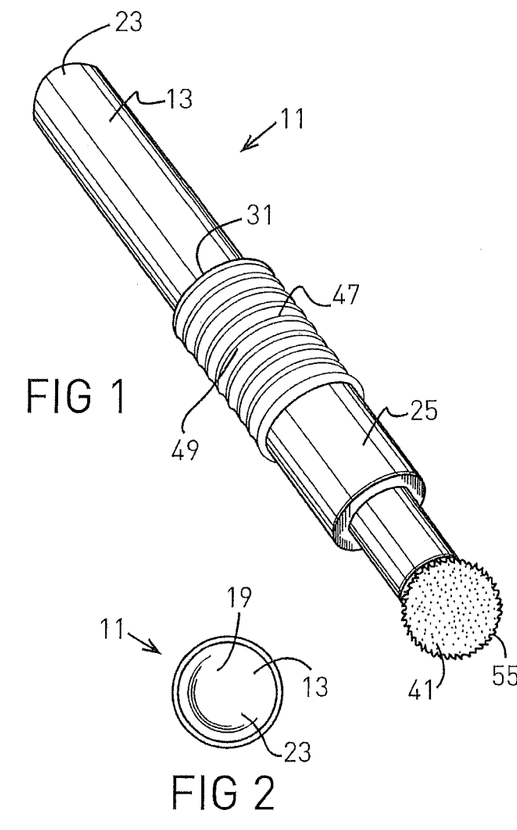
FIG. 1 is a view in perspective of a first embodiment of an applicator, constructed in accordance with my invention.
FIG. 2 is a bottom plan view of the applicator shown in FIG. 1.
Figure 3:
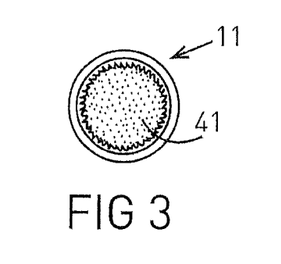
FIG. 3 is a top plan view of the applicator shown in FIG. 1.
Figure 4:
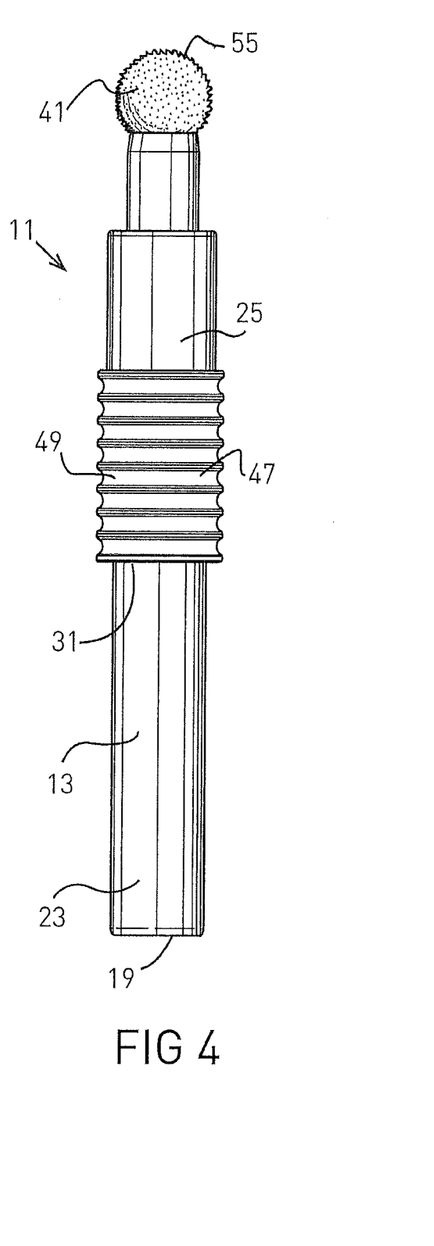
FIG. 4 is a front elevational view of the applicator shown in FIG. 1, the right side elevational view of the applicator shown in FIG. 1, the left side elevational view of the applicator shown in FIG. 1, and the rear elevational view of the applicator shown in FIG. 1 all being the same as the front elevational view of the applicator shown in FIG. 1.
Figures 5, 6:
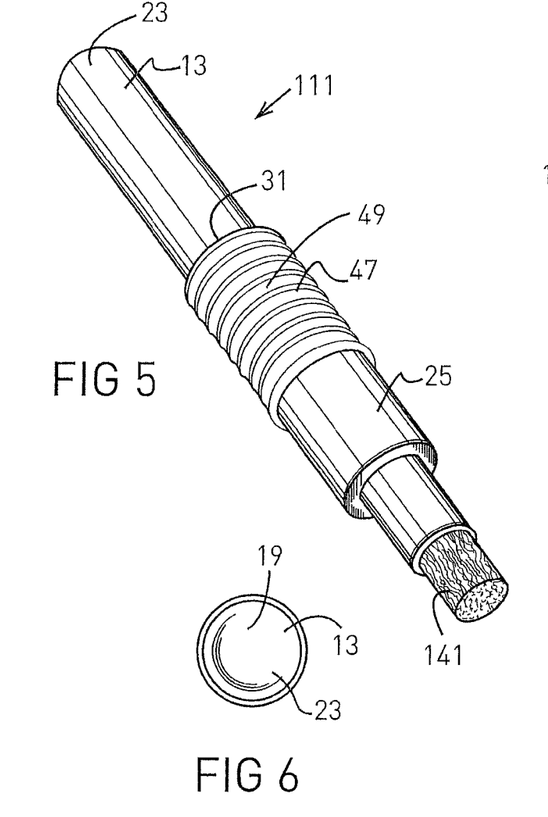
FIG. 5 is a view in perspective of a second embodiment of an applicator, constructed in accordance with my invention.
FIG. 6 is a bottom plan view of the applicator shown in FIG. 5.
Figure 7:
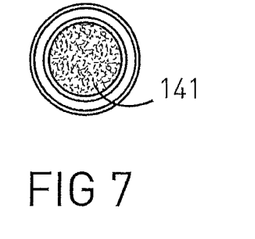
FIG. 7 is a top plan view of the applicator shown in FIG. 5.
Figure 8:
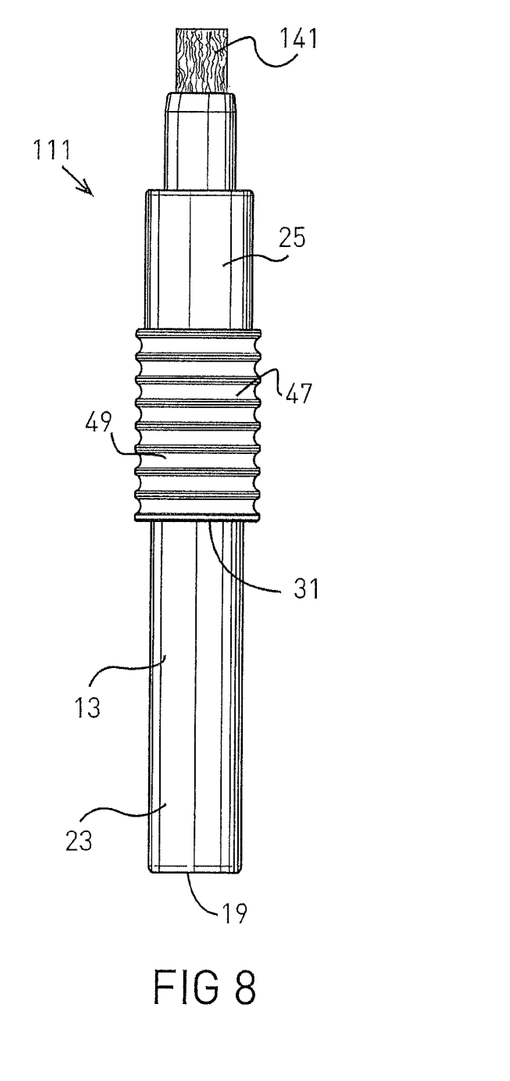
FIG. 8 is a front elevational view of the applicator shown in FIG. 5, the right side elevational view of the applicator shown in FIG. 5, the left side elevational view of the applicator shown in FIG. 5, and the rear elevational view of the applicator shown in FIG. 5 all being the same as the front elevational view of the applicator shown in FIG. 5.
Figures 9, 10:
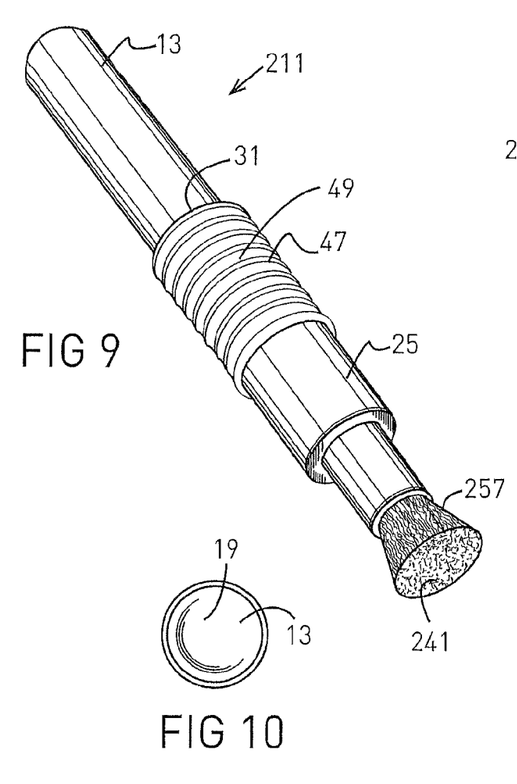
FIG. 9 is a view in perspective of a third embodiment of an applicator, constructed in accordance with my invention.
FIG. 10 is a bottom plan view of the applicator shown in FIG. 9.
Figure 11:
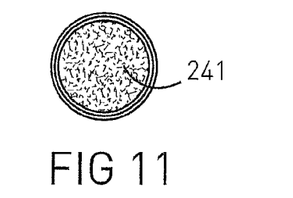
FIG. 11 is a top plan view of the applicator shown in FIG. 9.
Figure 12:
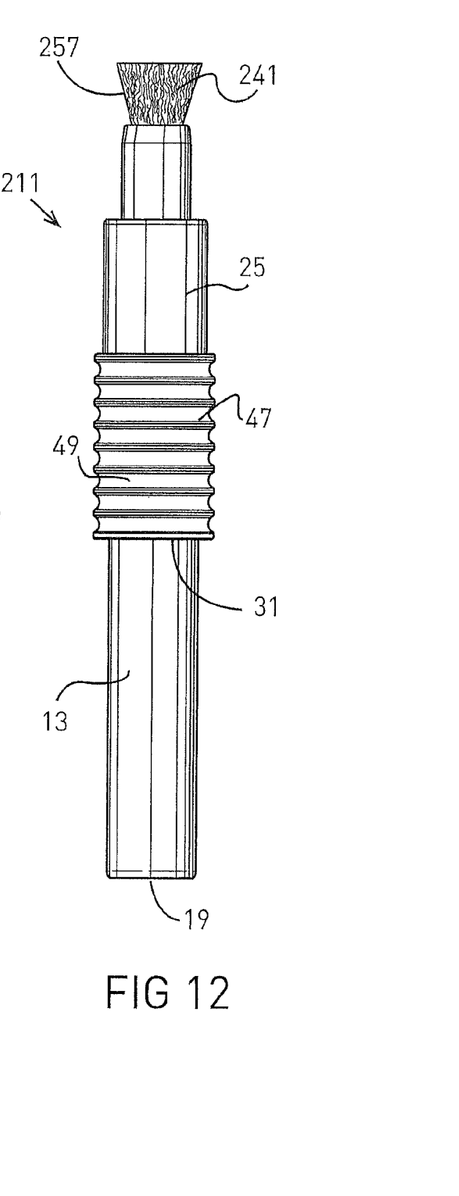
FIG. 12 is a front elevational view of the applicator shown in FIG. 9, the right side elevational view of the applicator shown in FIG. 9, the left side elevational view of the applicator shown in FIG. 9, and the rear elevational view of the applicator shown in FIG. 9 all being the same as the front elevational view of the applicator shown in FIG. 9.
Figures 13, 14:
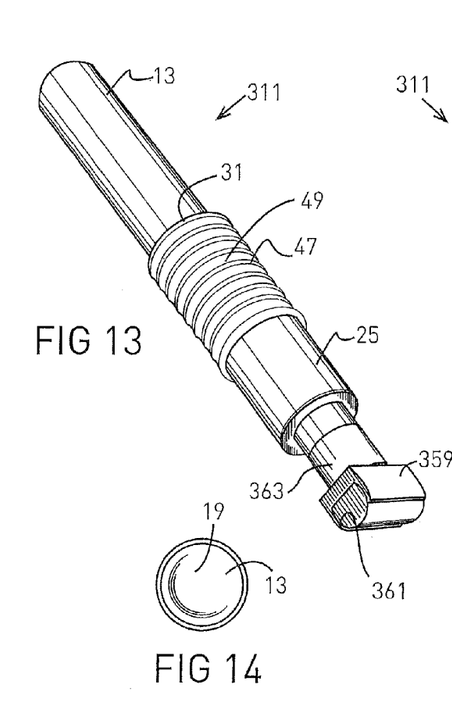
FIG. 13 is a view in perspective of a fourth embodiment of an applicator, constructed in accordance with my invention.
FIG. 14 is a bottom plan view of the applicator shown in FIG. 13.
Figure 15:
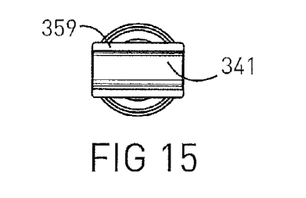
FIG. 15 is a top plan view of the applicator shown in FIG. 13.
Figures 16, 17:
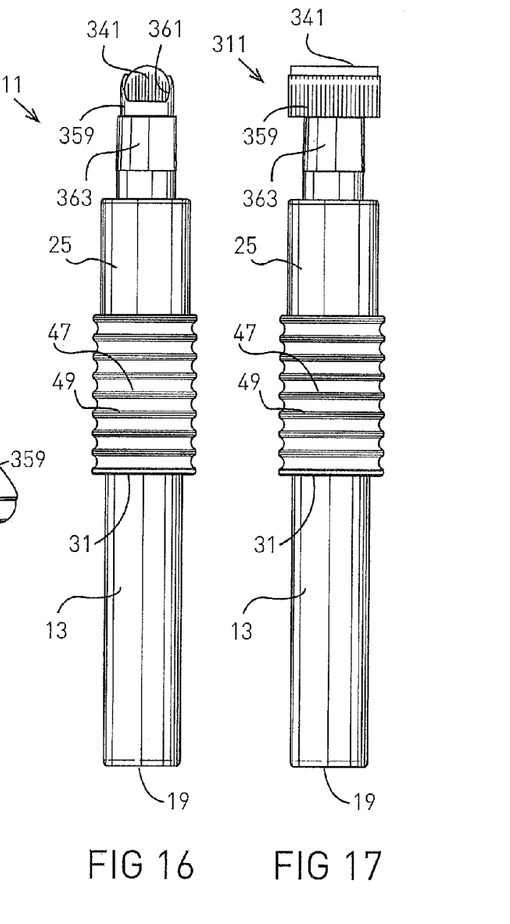
FIG. 16 is a right side elevational view of the applicator shown in FIG. 13, the left side elevational view of the applicator shown in FIG. 13 being the same as the right side elevational view of the applicator shown in FIG. 13.
FIG. 17 is a front elevational view of the applicator shown in FIG. 13, the rear elevational view of the applicator shown in FIG. 13 being the same as the front elevational view of the applicator shown in FIG. 13.
Figures 18, 19:
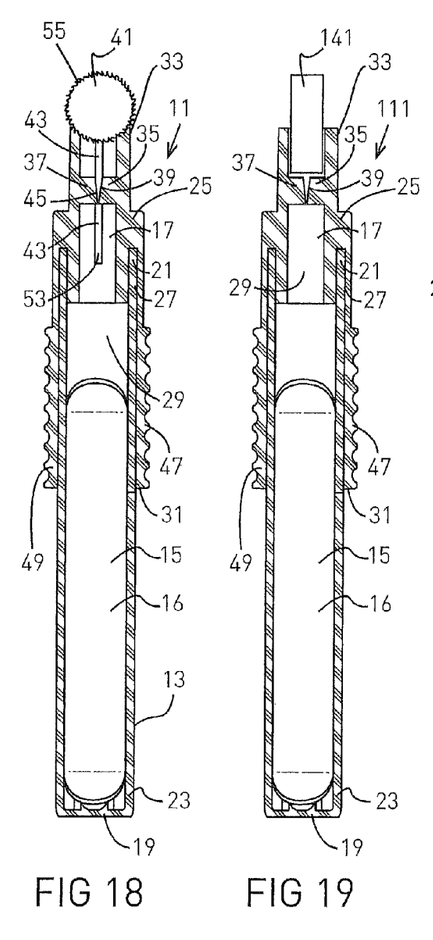
FIG. 18 is a view in cross-section taken along the lines and arrows 18-18 shown in FIG. 4.
FIG. 19 is a view in cross-section taken along the lines and arrows 19-19 shown in FIG. 8.
Figure 20:
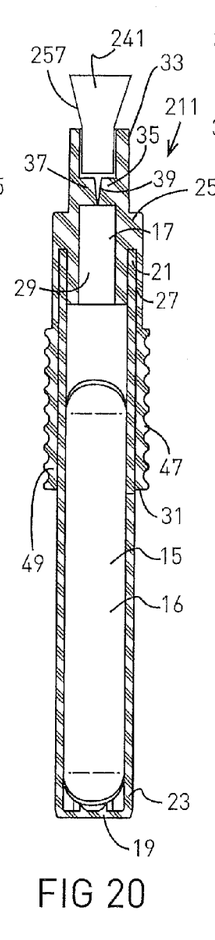
FIG. 20 is a view in cross-section taken along the lines and arrows 20-20 shown in FIG. 12.
Figure 21:
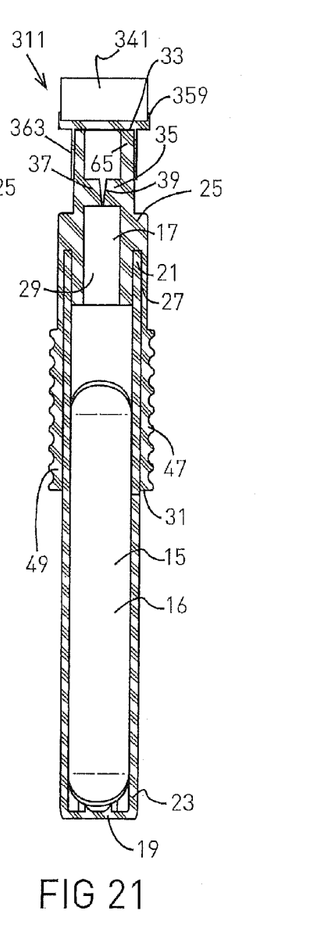
FIG. 21 is a view in cross-section taken along the lines and arrows 21-21 shown in FIG. 16.
Figure 22:
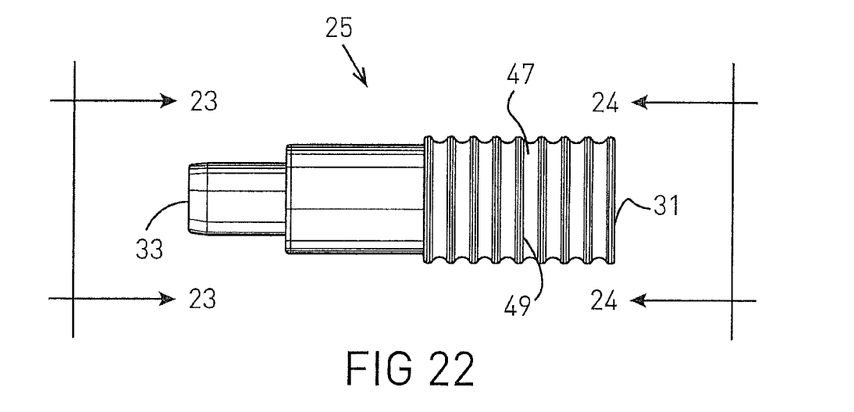
FIG. 22 is a view in elevation of the dispensing member 25, constructed in accordance with the invention, prior to a dauber being mounted thereon.
Figure 23:
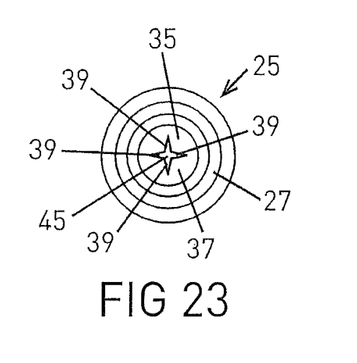
FIG. 23 is a view in cross-section taken along the lines and arrows 23-23 shown in FIG. 22.
Figure 24:
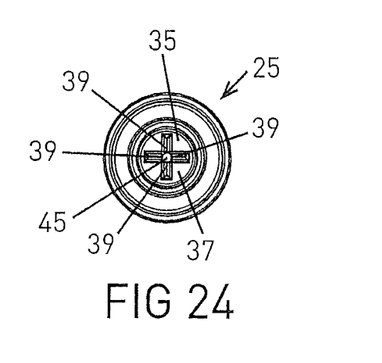
FIG. 24 is a view in cross-section taken along the lines and arrows 24-24 shown in FIG. 22.
Figure 25:
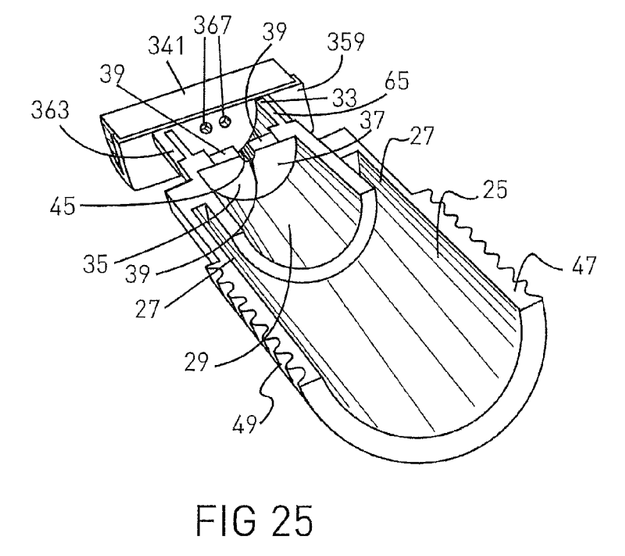
FIG. 25 is a perspective view showing a cross-section of the dispensing member 325, constructed in accordance with the invention.
Figure 26:
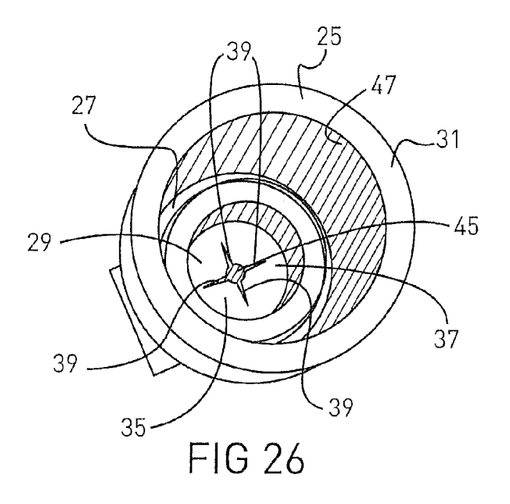
FIG. 26 is a view in perspective of the dispensing member 325, constructed in accordance with the invention, oriented to highlight the interior of the dispensing member 325 when viewed from the first end 331 of the dispensing member 325.
Figures 27, 28, 29:
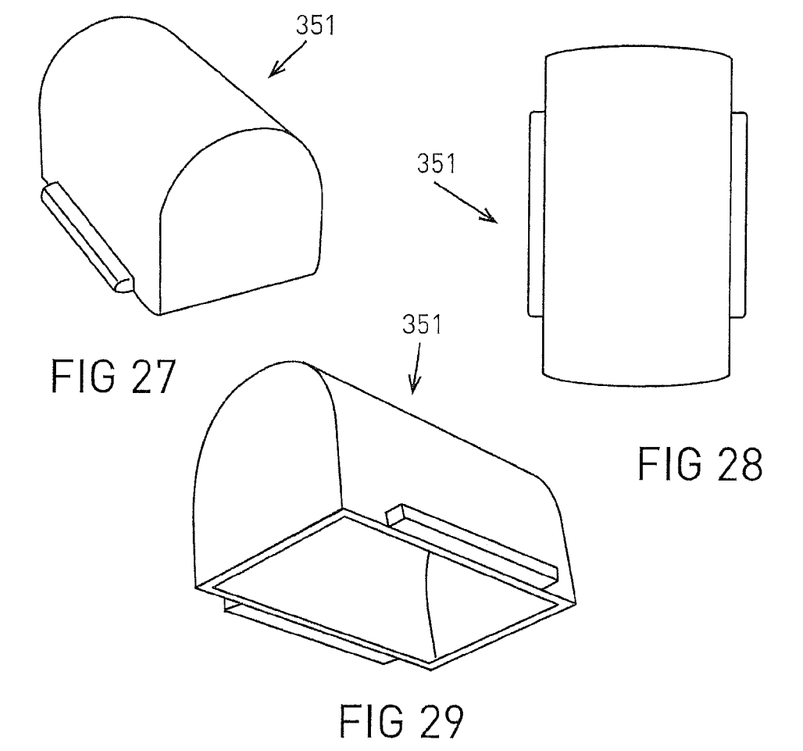
FIG. 27 is a view in perspective of a hollow cap, constructed in accordance with the invention, that may be used in connection with the applicator shown in FIGS. 13, 16, and 17.
FIG. 28 is a top plan view of the cap of FIG. 27.
FIG. 29 is another view in perspective of the cap of FIG. 27, oriented to highlight the structure of the cap when viewed from below and to the side of the cap.

The tube 13 has an open end 17, a closed end 19, a first end portion 21, and a second end portion 23, and the open end 17 of the tube 11 is located in the first end portion 21 of the tube 11.

The crushable glass ampoule 15 is positioned in the tube 13, and the ampoule 15 preferably is constructed of glass of well known type such as onion skinned glass, which is chemically inert to the fluid 16 contained therein. The fluid 16 may be any desired fluid, including fluid having solids suspended therein. For example, fluid 16 may be adhesion promoting primers containing isocyanates, which may contain carbon back suspended solids. Another example of fluid 16 is an adhesive containing cyanoacrylate. Preferably, the ampoule 15 is hermetically sealed and preferably is provided with an anhydrous inert gas head (not shown) over the fluid 16.

Applicator 11 also has a dispensing member 25 which mounts onto the tube 13 to form a sealed connection therebetween. Preferably, the sealed connection between the dispensing member 25 and the tube 13 is a sealed press-fit connection created by inserting the first end portion 21 of the tube 13 tightly into an annular slot 27 formed in the dispensing member 25. The dispensing member 25, which is preferably substantially cylindrical in shape and which is preferably constructed from a deformable, pliable material, such as a plastic material such as a chemically inert resin such as polyethylene resins or ethylvinylacetate, or olefinic thermoplastic elastomers, via injection molding, is capable of being deformed by finger pressure of the user of the applicator 11, and preferably returns to its original shape upon pressure release. The dispensing member 25 has a passageway 29 extending through it from the first end 31 of the dispensing member 25 to the second end 33 of the dispensing member 25. The passageway 29 is in fluid communication with the open end 17 of the tube 13 when the dispensing member 25 is mounted on the first end portion 21 of the tube 13, thereby permitting fluid 16 to flow from the open end 17 of the tube 13 into the passageway 29 formed in the dispensing member 25 after the crushable glass ampoule 15 containing the fluid 16 has been crushed within the tube 13.

Preferably, a valve 35 is located within the passageway 25 to control the flow of fluid 16 to the second end 33 of the dispensing member 25 when the applicator 11 has been assembled and put into use. In this embodiment of the invention, the valve 35 is a disk 37 that extends across the passageway 29 and has cutaway portions 39 formed therein and extending completely through the disk 37 for permitting fluid 16 to flow through the disk 37 via the cutaway portions 39 so that fluid 16 may flow from the open end 17 of the tube 13 (after the ampoule 15 positioned in the tube 13 has been crushed to release the fluid 16 from the ampoule 15) into the passageway 29, through the valve 35 via the cutaway portions 39, and to the second end 33 of the dispensing member 25. Preferably, the disk 37 is integrally formed into the dispensing member 25 during the injection molding of the dispensing member 25.

The dispensing member 25 has a dauber 41, which mounts onto the second end 33 of the dispensing member 25, and into which fluid 16 from the tube 13 after the crushable glass ampoule 15 has been crushed within the tube 13 may flow via the passageway 29 of the dispensing member 25 when the applicator 11 is assembled and put into use. In this embodiment of the invention, the dauber 41 preferably comprises a sphere preferably comprised of wool fibers, or fiber strands of any suitable synthetic material (such as polyester fibers) that are compatible with the fluid 16. Referring to FIG. 18, to secure the dauber 41 to the second end 33 of the dispensing member 25, strands of fibers of the dauber 41 are threaded through an eye (not shown) formed in one end portion of a needle-like member 43, and the needle-like member 43 is inserted into an opening 45 extending through the disk 37 forming a press-fit connection between the disk 37 and the needle-like member 43.

The dispensing member 25 also has a skirt or band or sleeve 47, which preferably is integrally formed in the dispensing member 25, that surrounds a portion of the tube 13 when the applicator 11 is assembled. The skirt 47 has a gripping portion 49 that preferably may be gripped by and squeezed between the applicator 11 user's forefinger and thumb to cause the gripping portion 49 and the portion of the tube 13 surrounded thereby to move inwardly, thereby crushing the glass ampoule 15 contained within the tube 13 to release the fluid 16 contained in the ampoule 15, when the applicator 11 is assembled and ready to be put into use. The skirt 47 substantially blocks any glass shards created when the crushable glass amoule 15 is crushed from projecting outwardly from the applicator 11 at the gripping portion 49 of the skirt, thereby guarding against and minimizing the chances of a user of the applicator 11 being injured by the user's forefinger and/or thumb being cut by a glass shard from the crushed ampoule 15 projecting outwardly through the applicator 11 at the gripping portion 49 when the applicator 11 is subsequently squeezed inwardly at the gripping portion 49 of the skirt 47 between the user's forefinger and thumb to cause the fluid 16 released from the glass ampoule 15 to flow from the tube 13 to and through the passageway 29 to the dauber 41 and be metered out from the dauber 41 onto a surface.

The applicator 11 may be assembled by placing an ampoule 15 containing a fluid 16 therein into the tube 13. Then, the first end portion 21 of the tube 13 is inserted into the annular slot 27 (see FIGS. 18 and 24) formed in the dispensing member 25 to mount the dispensing member 25 on the tube 13 and form a sealed press-fit connection therebetween. Referring to FIG. 18, the dauber 41 is mounted onto the second end 33 of the dispensing member 25 by threading strands of fibers of the dauber 41 through the eye formed in one end portion of the needle-like member 43 and inserting the other end portion 53 of the needle-like member 43 into and through the opening 45 extending through the disk 37, forming a press-fit connection between the disk 37 and the needle-like member 43, until the dauber 41 is flushed against the second end portion 33 of the dispensing member 25 covering the exit from the passageway 29 at the second end 33 of the dispensing member 25.

In use, the applicator 11, after being assembled, may be squeezed inwardly at the gripping portion 49, preferably by squeezing the gripping portion 49 between the forefinger and thumb of the user of the applicator 11, to cause the gripping portion 49 and the portion of the tube 13 surrounded thereby to move inwardly, thereby crushing the glass ampoule 15 contained within the tube 13 to release the fluid 16 contained in the ampoule 15. After the fluid 16 is released from the ampoule 15, the applicator 11 may be squeezed inwardly again at the gripping portion 49 of the skirt 47 between the user's forefinger and thumb to cause the fluid 16 to flow from the open end 17 of the tube 13 into the passageway 29 that extends through the dispensing member 25, through the passageway 29 past the valve 35 via the cutaway portions 39 in the disk 37, to the second end 33 of the dispensing member 25 and into the dauber 41 from where the fluid 16 may be applied from an outer surface 55 of the dauber 41 to a surface by brushing the dauber 41 over such surface.

By squeezing at the gripping portion 49 of the skirt 47 of the dispensing member 25 between the user's forefinger and thumb to cause the fluid 16 released from the ampoule 15 to flow to the dauber 41 and be metered out from the dauber 41 onto a surface, the user of the applicator 11 is protected from injury since the skirt 47 guards against and minimizes the chances of the user being cut by glass shards, created when the ampoule 15 is crushed, by substantially blocking any such glass shards from penetrating outwardly from the applicator 11 at the location of the skirt 47.

To accommodate various amounts of fluid fills (that is, different volumetric amounts of fluid 16) in the applicator 11, tubes 13 of different lengths may be used to permit different lengths of ampoules 15 to be housed within the applicator 11 so that the amount of fluid 16 to be held within the applicator 11 may be pre-set as desired. For instance, to obtain a large fluid fill in the applicator 11, a tube 13 having a long length may be used to accommodate a long ampoule 15 having a large amount of fluid 16 contained therein, and, for instance, to obtain a small fluid fill in the applicator 11, a tube 13 having a short length may be used to accommodate a short ampoule 15 having a small amount of fluid 16 contained therein. However, no matter what length tube 13 is used, the same guard head, that is, the same dispensing member 25 having the protective skirt 47 may be used.

Turning now to FIGS. 5-8, 19, and 22-24, there is shown a second embodiment of the invention. Here, the inventive applicator 111 is substantially the same as the applicator 11, except that a cylindrical dauber 141 is used in the applicator 111 rather than the dauber 41 and needle-like member 43 used in the applicator 11. Preferably, the cylindrical dauber 141 comprises a plurality of fiber strands, in side by side relation forming a porous cylindrical structure. The fiber strands are of any suitable synthetic material, such as polyester fiber, compatible with the fluid 16 to be carried and dispensed from the applicator 111. The dauber 141 preferably is mounted on the second end 33 of the dispensing member 25 by press-fitting a portion of the dauber 141 into the passageway 29 at the second end 33 of the dispensing member 25 so that a portion of the dauber 141 protrudes from the passageway 29. Also, an adhesive may be applied between a portion of dauber 141 and the portion of the dispensing member 25 that forms the passageway 29 at the second end 33 of the dispensing member 25 to mount the dauber 141 onto the dispensing member 25. The applicator 111 operates in substantially the same manner as the applicator 11.

Figure 30:
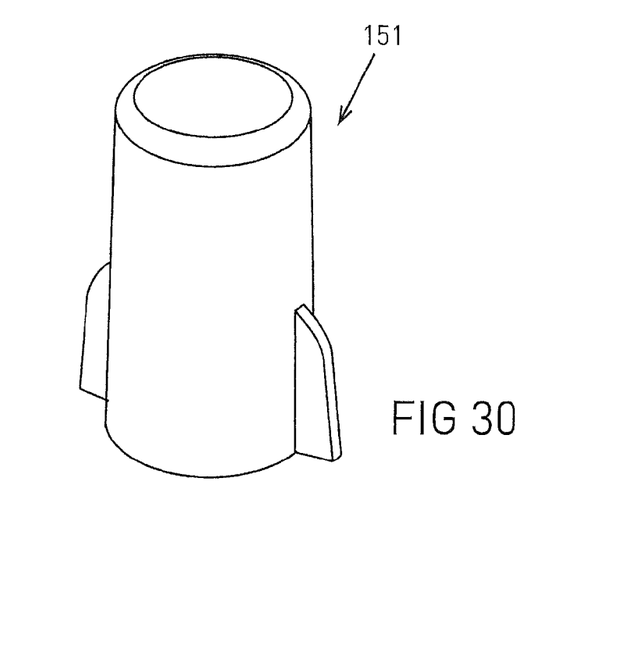
FIG. 30 is a view in perspective of a cap, constructed in accordance with the invention, that may be used in connection with the applicators shown in FIGS. 5 and 8.
Figure 31:
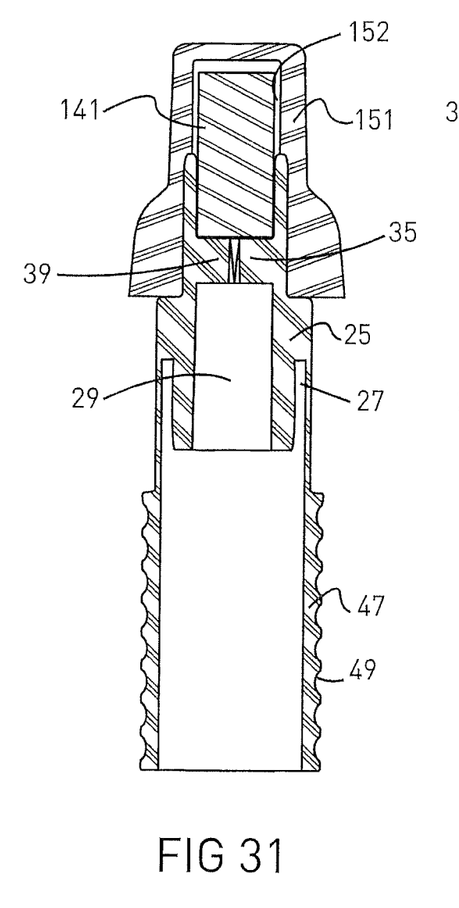
FIG. 31 is a view in cross-section showing the cap of FIG. 30 secured onto the second end of the dispensing member 25 of the applicator 111 shown in FIGS. 5 and 8 and covering the dauber 141 of the applicator 111 to seal the dauber 141 from the air.

In this embodiment of the invention, a hollow cap 151, which is shown in FIGS. 30 and 31, may be used in conjunction with the applicator 111. The hollow cap 151 may be placed onto the second end 33 of the dispensing member 25 and over the dauber 141 to seal the dauber 141 from the air, thereby permitting fluid 16 to be dispensed from the applicator 111 on multiple occasions after the ampoule 151 has been crushed. Preferably, the cap 151 is made from a plastic material, such as a polyolefin elastomer such as acetal, using injection molding. Preferably, in this embodiment of the invention, the cap 151 is sized to exclude or substantially minimize exposure of the dauber 141 to the atmosphere when the cap 151 is secured in place on the applicator 111 covering the dauber 141, thereby guarding against the dauber 141 drying out and/or guarding against an undesired chemical reaction occurring due to the fluid 16 in the dauber 141 being exposed to air between uses of the applicator 111. Specifically, the cap 151 preferably is sized such that its interior space 152 conforms to or substantially matches the outer surfaces of the dauber 141 and the portion of the applicator 111 that surrounds the dauber 141 and holds the dauber 141 in place to substantially eliminate any air space between the dauber 141 and the cap 151 when the cap 151 is secured in place on the applicator 111 covering the dauber 141.

If not all of the fluid 16 has been dispensed from the applicator 111 when the applicator 111 is first used, the cap 151 may be press-fit over the second end 33 of the dispensing member 25 covering the dauber 141 to seal the dauber 141 from the air, thereby permitting the fluid 16 that remains in the applicator 111 to be applied to a surface at a later time by removing the cap 151 and applying such fluid to a surface by again squeezing the gripping portion 49 of the skirt 47 to cause fluid 16 to be dispensed from the applicator 111 via the dauber 141 onto such surface. The cap 151 may also be placed over the second end 33 of the dispensing member 25 covering the dauber 141 to protect the dauber 141 from dirt and the like until the applicator 111 is put into use, at which time the cap 151 is removed from the applicator 111.

Turning now to FIGS. 9-12, 20, and 22-24, there is shown a third embodiment of the invention. Here, the inventive applicator 211 is substantially the same as the applicator 111, except that a dauber 241 is used in the applicator 211 rather than the dauber 141 used in the applicator 111. Preferably, the dauber 241 is the same as the dauber 141, except the end portion 257 of the dauber 241 flares radially outwardly as shown in the drawings. The structure of dauber 241 is described in detail in my U.S. Pat. No. 7,004,657, which is hereby incorporated herein by reference. The dauber 241 is mounted on the applicator 211 in the same manner that the dauber 141 is mounted on the applicator 111. The applicator 211 operates in substantially the same manner as the applicator 111.

Turning now to FIGS. 13-17, 21, and 22-26, there is shown a fourth embodiment of the invention. Here, the invention applicator 311 is substantially the same as the applicator 111, except that a dauber 341 is used in the applicator 311 rather than the dauber 141 used in the applicator 111, and a dauber holding device 359 is used in the applicator 311 for holding the dauber 341 and for mounting the dauber 341 onto the dispensing member 25 of the applicator 311. In this embodiment of the invention, the dauber 341 is substantially a larger version of the dauber 141, which preferably is mounted onto the dauber holding device 359 by being press-fit into an trough-like shaped or up-side-down saddle shaped portion 361 of the dauber holding device 359. An adhesive also may be used between the dauber 341 and the portion 361 of the dauber holding device 359 to hold the dauber 341 in place. The dauber holding device 359 also has a cylindrical hollow tube portion 363 that is integral with and extends away from the portion 361, and the tube portion 363 is shaped and sized to be mounted over the end portion 65 of the dispensing member 25 to create a tight press-fit sealed connection therebetween. The dauber holding device 359 is provided with at least one hole 367 (there being two such holes 367 shown in FIG. 25) extending through the trough-like shaped portion 361 of the dauber holding device 359 through which fluid 16 may flow from the passageway 29 at the second end 33 of the dispensing member 25 into the dauber 341 when the applicator 311 is in use. The applicator 311 operates in substantially the same manner as the applicator 111.

In this embodiment of the invention, a hollow cap 351, shown in FIGS. 27-29, and 32, may be press-fit over the outside of the portion 361 of the dauber holding device 359, thereby covering the dauber 341, when desired, to seal the dauber 341 from the air, thereby permitting fluid 16 to be dispensed from the applicator 311 on multiple occasions after the ampoule 351 has been crushed. Preferably, the cap 351 is made from resin materials such as a polyolefin elastomer such as acetal, using injection molding. Preferably, in this embodiment of the invention, the cap 351 is sized to exclude or substantially minimize exposure of the dauber 341 to the atmosphere when the cap 351 is secured in place on the applicator 311 covering the dauber 341, thereby guarding against the dauber 341 drying out and/or guarding against an undesired chemical reaction occurring due to the fluid 16 in the dauber 341 being exposed to air between uses of the applicator 311. Specifically, the cap 351 preferably is sized such that its interior space 352 conforms to or substantially matches the outer surfaces of the dauber 341 and the portion of the applicator 311 that surrounds the dauber 341 and holds the dauber 341 in place to substantially eliminate any air space between the dauber 341 and the cap 351when the cap 351 is secured in place on the applicator 311 covering the dauber 341.

Figure 32:
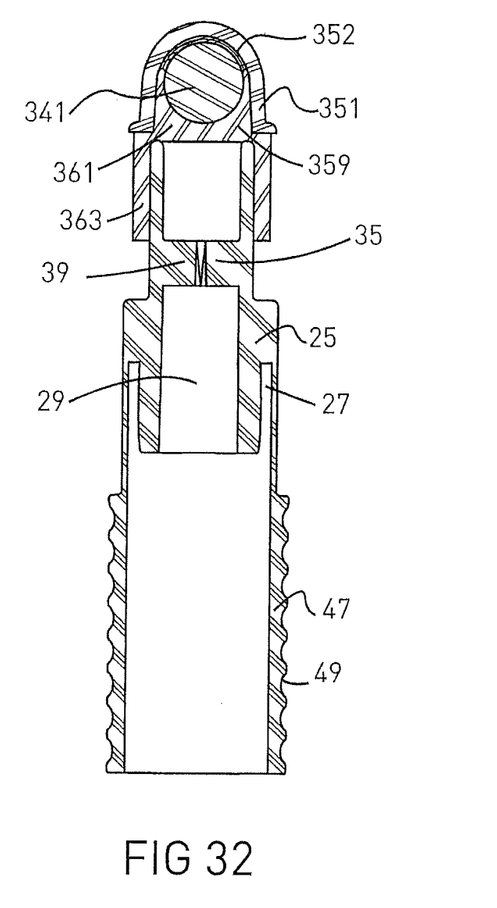
FIG. 32 is a view in cross-section showing the cap of FIGS. 27, 28, and 29 secured onto the second end of the dispensing member 25 of the applicator 311 shown in FIGS. 13, 16, and 17 and covering the dauber 341 to seal the dauber 341 from the air.

If not all of the fluid 16 has been dispensed from the applicator 311 when the applicator 311 is first used, the cap 351 may be press-fit over the second end 33 of the dispensing member 25 covering the dauber 341 to seal the dauber 341 from the air, thereby permitting the fluid 16 that remains in the applicator 311 to be applied to a surface at a later time by removing the cap 351 and applying such fluid to a surface by again squeezing the gripping portion 49 of the skirt 47 to cause fluid 16 to be dispensed from the applicator 311 via the dauber 341 onto such surface. The cap 351 may also be placed over the second end 33 of the dispensing member 25 covering the dauber 341 to protect the dauber 341 from dirt and the like until the applicator 311 is put into use, at which time the cap 351 is removed from the applicator 311.

The dauber holding device 359 preferably is made from a plastic material, such as a chemically inert resin such as a polyolefin elastomer such as acetal, using injection molding.

The invention claimed is:

1. An applicator for dispensing fluid therefrom and applying said fluid to a surface, comprising:
  a deformable tube for holding a crushable glass ampoule containing a fluid to be dispensed from the applicator, the deformable tube having an open end, a closed end, a first end portion, and a second end portion, the open end of the tube being located in the first end portion of the tube,
  a crushable glass ampoule positioned in the deformable tube, the crushable glass ampoule containing fluid to be dispensed from the applicator,
  a dispensing member mounted on the tube creating a sealed connection therebetween, the dispensing member having a first end and a second end,
  the dispensing member having a passageway extending therethrough from the first end of the dispensing member to the second end of the dispensing member for dispensing fluid from the open end of the tube after the crushable glass ampoule containing fluid has been crushed within the tube, the passageway extending through the dispensing member being in fluid communication with the open end of the tube,
  the dispensing member including a dauber mounted thereon into which fluid from the tube after the crushable glass ampoule has been crushed within the tube may flow via the passageway of the dispensing member, the dauber having at least a portion thereof projecting from the passageway at the second end of the dispensing member, and the dauber having a surface on the portion thereof that projects from the passageway at the second end of the dispensing member from which fluid that has flowed into the dauber from the tube via the passageway of the dispensing member may be applied to a surface, and
  the dispensing member having a skirt that surrounds a portion of the tube, the skirt having a portion for squeezing inwardly to cause the tube positioned thereunder to deform inwardly and crush the crushable glass ampoule positioned within the tube, thereby releasing the fluid contained in the crushable glass ampoule into the tube, and for blocking any glass shards created when the crushable glass ampoule is crushed from projecting outwardly from the applicator at said portion of the skirt.

2. The applicator of claim 1,
  the dispensing member having a slot formed therein into which the first end portion of the tube extends forming a press-fit connection therebetween.

3. The applicator of claim 1, the dauber being spherical in shape.

4. The applicator of claim 1, the dauber being cylindrical in shape.

5. The applicator of claim 1, the dauber having a central axis, the dauber having a cylindrical first end portion that is located within the passageway at the second end of the dispensing member, and the dauber having a second end portion that projects beyond the second end of the dispensing member and flares radically outwardly away from the central axis of the dauber.

6. The applicator of claim 1, further including a dauber holding device for holding the dauber and for mounting the dauber onto the dispensing member, the dauber being mounted on a trough-like shaped portion of the dauber holding device, the dauber holding device having a hollow tube portion that is integral with and extends away from the trough-like shaped portion of the dauber holding device that is shaped and sized to be mounted over the dispensing member at the first end of the dispensing member to create a tight press-fit sealed connection therebetween, and the dauber holding device having at least one hole extending through the trough-like shaped portion of the dauber holding device through which fluid may flow from the passageway at the second end of the dispensing member into the dauber when the applicator is in use.

7. The applicator of claim 1, further including a hollow cap whose interior space substantially matches the outer surfaces of the dauber and the portion of the applicator that surrounds and holds the dauber in place to substantially eliminate any air space between the dauber and the cap when the cap is secured in place on the applicator covering the dauber.

8. The applicator of claim 1, wherein said dispensing member is coextensive with at least a portion of said tube, and wherein said tube open is secured within an annular slot of said dispensing member.

9. The applicator of claim 1, wherein said tube includes a first portion that is not axially coextensive with said dispensing member, wherein said tube includes a second portion that is axially coextensive with said dispensing member, and wherein said passageway of said dispensing member includes a first portion that is axially coextensive with said axially coextensive tube second portion, and a second portion that is axially coextensive with said dispensing member and which is not axially coextensive with said tube.

10. An applicator for dispensing fluid therefrom and applying said fluid to a surface, comprising:
    a deformable tube for holding a crushable glass ampoule containing a fluid to be dispensed from the applicator, the deformable tube having an open end, a closed end, a first end portion, and a second end portion, the open end of the tube being located in the first end portion of the tube,
    a crushable glass ampoule positioned in the deformable tube, the crushable glass ampoule containing fluid to be dispensed from the applicator,
    a dispensing member mounted on the tube creating a sealed connection therebetween, the dispensing member having a first end and a second end,
    the dispensing member having a passageway extending therethrough from the first end of the dispensing member to the second end of the dispensing member for dispensing fluid from the open end of the tube after the crushable glass ampoule containing fluid has been crushed within the tube, the passageway extending through the dispensing member being in fluid communication with the open end of the tube,
    the dispensing member including a dauber mounted thereon into which fluid from the tube after the crushable glass ampoule has been crushed within the tube may flow via the passageway of the dispensing member, the dauber having at least a portion thereof projecting from the passageway at the second end of the dispensing member, and the dauber having a surface on the portion thereof that projects from the passageway at the second end of the dispensing member from which fluid that has flowed into the dauber from the tube via the passageway of the dispensing member may be applied to a surface, and
    a band surrounding a portion of the tube, the band having a portion for squeezing inwardly to cause the tube positioned thereunder to deform inwardly and crush the crushable glass ampoule positioned within the tube, thereby releasing the fluid contained in the crushable glass ampoule into the tube, and for blocking any glass shards created when the crushable glass ampoule is crushed from projecting outwardly from the applicator at said portion of the band.

11. The applicator of claim 10,
    the dispensing member having a slot formed therein into which the first end portion of the tube extends forming a press-fit connection therebetween.

12. The applicator of claim 10, the dauber being spherical in shape.

13. The applicator of claim 10, the dauber being cylindrical in shape.

14. The applicator of claim 10, the dauber having a central axis, the dauber having a cylindrical first end portion that is located within the passageway at the second end of the dispensing member, and the dauber having a second end portion that projects beyond the second end of the dispensing member and flares radically outwardly away from the central axis of the dauber.

15. The applicator of claim 10, further including a dauber holding device for holding the dauber and for mounting the dauber onto the dispensing member, the dauber being mounted on a trough-like shaped portion of the dauber holding device, the dauber holding device having a hollow tube portion that is integral with and extends away from the trough-like shaped portion of the dauber holding device that is shaped and sized to be mounted over the dispensing member at the first end of the dispensing member to create a tight press-fit sealed connection therebetween, and the dauber holding device having at least one hole extending through the trough-like shaped portion of the dauber holding device through which fluid may flow from the passageway at the second end of the dispensing member into the dauber when the applicator is in use.

16. The applicator of claim 10, further including a hollow cap whose interior space substantially matches the outer surfaces of the dauber and the portion of the applicator that surrounds and holds the dauber in place to substantially eliminate any air space between the dauber and the cap when the cap is secured in place on the applicator covering the dauber.

17. An applicator assembly for dispensing fluid therefrom and applying said fluid to a surface, comprising:
    a deformable tube for holding a crushable glass ampoule containing a fluid to be dispensed from the applicator assembly when assembled, the deformable tube having an open end, a closed end, a first end portion, and a second end portion, the open end of the tube being located in the first end portion of the tube,
    a dispensing member mountable on the tube, the dispensing member having a first end and a second end, a seal being formed between the tube and the dispensing member when the dispensing member is mounted on the tube,
    the dispensing member having a passageway extending therethrough from the first end of the dispensing member to the second end of the dispensing member for dispensing fluid from the open end of the tube after a crushable glass ampoule containing fluid has been crushed within the tube, the passageway extending through the dispensing member being in fluid communication with the open end of the tube when mounted on the tube,
    the dispensing member including a dauber mountable thereon into which fluid from the tube after a crushable glass ampoule containing fluid has been crushed within the tube may flow via the passageway of the dispensing member, the dauber having at least a portion thereof projecting from the passageway at the second end of the dispensing member when the dauber is mounted on the dispensing member, and the dauber having a surface from which fluid that has flowed into the dauber from the tube via the passageway of the dispensing member may be applied to a surface, and the dispensing member having a skirt that surrounds a portion of the tube when the dispensing member is mounted on the tube, the skirt having a portion for squeezing inwardly to cause the tube positioned thereunder when the dispensing member is mounted on the tube to deform inwardly and crush a crushable glass ampoule when positioned within the tube and for blocking any glass shards created when the crushable glass ampoule is crushed from projecting outwardly at said portion of the skirt from the applicator assembly when assembled.

18. The applicator assembly of claim 17, further including a crushable glass ampoule to be positioned in said deformable tube, the crushable glass ampoule containing fluid to be dispensed from the applicator.

19. The applicator assembly of claim 17, the dispensing member having a slot formed therein into which the first end portion of the tube extends when the dispensing member is mounted on the tube forming a press-fit connection therebetween.

20. The applicator of claim 17, the dauber being spherical in shape.

21. The applicator of claim 17, the dauber being cylindrical in shape.

22. The applicator of claim 17, the dauber having a central axis, the dauber having a cylindrical first end portion that is located within the passageway at the second end of the dispensing member, and the dauber having a second end portion that projects beyond the second end of the dispensing member and flares radically outwardly away from the central axis of the dauber.

23. The applicator of claim 17, further including a dauber holding device for holding the dauber and for mounting the dauber onto the dispensing member, the dauber being mounted on a trough-like shaped portion of the dauber holding device, the dauber holding device having a hollow tube portion that is integral with and extends away from the trough-like shaped portion of the dauber holding device that is shaped and sized to be mounted over the dispensing member at the first end of the dispensing member to create a tight press-fit sealed connection therebetween, and the dauber holding device having at least one hole extending through the trough-like shaped portion of the dauber holding device through which fluid may flow from the passageway at the second end of the dispensing member into the dauber when the applicator is in use.

24. The applicator assembly of claim 17, further including a variety of tubes of different lengths and a variety of ampoules having various fluid fill amounts.

25. The applicator of claim 17, further including a hollow cap whose interior space substantially matches the outer surfaces of the dauber and the portion of the applicator that surrounds and holds the dauber in place to substantially eliminate any air space between the dauber and the cap when the cap is secured in place on the applicator covering the dauber.

* * * * *